United States Patent [19]

Mattson et al.

[11] Patent Number: 4,738,987
[45] Date of Patent: Apr. 19, 1988

[54] COMPOSITION FOR SKIN CARE

[75] Inventors: Roy D. Mattson; Reynold E. Holmen, both of White Bear Lake, Minn.

[73] Assignee: Kemsearch, Inc., Onamia, Minn.

[21] Appl. No.: 776,486

[22] Filed: Sep. 16, 1985

[51] Int. Cl.$^4$ .......................... A61K 7/40; A61K 7/48
[52] U.S. Cl. ............................. 514/770; 252/DIG. 5; 514/846
[58] Field of Search .............................. 514/846, 770; 252/DIG. 5

[56] References Cited

U.S. PATENT DOCUMENTS 1,623,340  4/1927  Hanson ........................ 252/DIG. 5

OTHER PUBLICATIONS

Bennett, Cosmetic Formulary, 1937, pp. 42–44, 48, 63, 96, 98, 102 and 103.

Primary Examiner—Dale R. Ore
Attorney, Agent, or Firm—Jacobson and Johnson

[57] ABSTRACT

A composition comprising the product of a homogeneous dispersion of water and the active components soap, a water-soluble alkali-metal silicate, and sulfonated castor oil and having a pH adjusted with acid to within the range of 6.5 to 10 for applying to the hands or other parts of the body to protect the skin against the aid in removal of non-water-soluble contaminants or soil.

18 Claims, No Drawings 4,738,987

COMPOSITION FOR SKIN CARE

BACKGROUND OF THE INVENTION

1. Field of the Invention

This invention relates generally to skin care and more particularly is directed toward an improved composition and method for protecting and cleaning skin, especially the hands of persons who work with non-water-soluble materials such as paints, lacquers, inks, pigments, metals, fiberglassed plastic layups, grease, oil, etc., and who otherwise use hazardous materials for cleansing their hands.

2. Background Art

It is well known that people working with any of the afore-mentioned materials have a problem in maintaining clean skin, especially the hands, without adversely affecting the condition of the skin. It very often is impractical, e.g. loss of dexterity or excessive perspiration, for the worker to wear protective gloves. Because of the extreme measures often necessary to effect adequate cleaning after exposure to the aforementioned types of contaminants, the skin may develop a very dry, taut feel which may be followed by skin cracks which then open the way to bleeding, even infection. Even without the latter end result, the dry and cracked skin presents an uncomfortable feel and an unsightly appearance. It becomes increasingly difficult to clean the skin; the soil or contaminant tends to remain in the cracks and crevices which have developed.

In lieu of total avoidance of direct contact with the described types of material, some means for aiding removal of the material has been utilized. Often this has taken the form of first washing the hands in a solvent such as kerosene, mineral spirits, or worse, gasoline or lacquer solvents. The hazards and deleterious effects of such procedures for cleansing are now too well known to need further description. Nevertheless, such dangerous practices continue even today. Two main types of compositions (herein designated as postapplied and preapplied, respectively) which have been used to reduce the described hazards associated with removal of soil or contaminants from the skin are described hereinbelow.

One commonly used postapplied type of composition for removing grease-borne soil, such as from the hands and arms of an automobile mechanic, is a gelled solvent vigorously applied to the soiled skin so as to disperse much of the grease before wiping it off with a cloth or paper towels, or before washing it off with soap and water. These gelled solvents typically are based on mineral spirits or light mineral oil gelled in a soap base comprised of oleic acid reacted with ammonia or an alkanolamine, for example. Sometimes small additions of a better solvent (such as pine oil), fragrances, and emollients are made. Mild abrasives, such as corn meal or pumice powder, may be added to improve soil removal action. Other additives, such as borax, trisodium phosphate or sodium polyphosphate may be used. One current product of this type contains fifteen ingredients and is relatively expensive.

A variant of the first type of cleansing aids is packaged in liquid form. In this variant a suitable solvent is dispersed or emulsified in a liquid soap composition and dispensed as a somewhat creamy lotion for application to the hands. Otherwise the mode of use and the effect are much the same as for the gelled solvent type. These two, representatives of the postapplied type, are not very effective on certain contaminants such as dried inks, paints and lacquers.

A second type is that of a cream or paste preapplied to the hands and rubbed in until the skin is left with an essentially dry, barely perceptible film of solids. This film serves as a barrier to reduce or prevent direct contact of the soil with the skin and as an aid to subsequent removal of the soil. The hands are later washed in the usual manner with water, with or without soap depending on the severity of the soil. The commonly used products representative of this type employ a soap-like base to which emollients may be added. A widely used example of this second type employs a sodium silicate and soap base to which glycerol has been added. It suffers from the distinct drawback of causing most skins to feel abnormally dry and taut. Unlike some members of the type preapplied to the skin, it has the virtue of being less prone to transfer deleterious traces to clean surfaces incidentally contacted by the hands thus coated. This is especially important when such surfaces have been cleaned and are ready for painting or other processing. Other cleansing aids, if used similarly, have been too prone to cause defects known as nonwets or fisheyes in the paint or lacquer coating or in other processing. They also usually have not offered as much aid in the subsequent removal of paint and lacquer from the skin.

The inadequacy of the prior art products to protect skin which is subjected to one or more of the enumerated types of occupational contaminants or soil and often to harsh cleaning procedures has a common consquence, i.e., the need for after-treatment of the skin with creams and lotions to restore softness and suppleness and prevent cracking and soreness. Such a procedure often falls short of the desired effect and also can be a distinct nuisance, especially because of the danger of contacting and recontaminating scrupulously cleaned surfaces. A number of prior art compositions of the two types mentioned are described in the *Chemical Formulary* by William Bennett, published by Chemical Publishing Company. Some 25 volumes of this work have been published from 1931 to 1983.

SUMMARY

The present invention provides a composition readily spreadable on the skin to form a barely perceptible barrier or coating having the combined properties of: (1) reducing subsequent direct and intimate contact of the skin by occupational contaminants or soils from non-water-soluble materials such as pigments, resins, metals, oils, greases, and non-aqueous inks, enamels, paints and lacquers; (2) aiding in the subsequent removal of such soil from the skin without need for using harsh or dangerous materials; (3) minimizing the transfer of deleterious traces from the hands to clean surfaces; and (4) aiding in maintaining the skin comfortably soft and supple in spite of the exposure to such non-water-soluble contaminants.

It is an object of this invention to provide such a composition and means in an economical and simple manner from readily available components having a history of safe use.

According to the teachings of this invention it has been found that a composition comprising the product of a mixture of water-soluble alkali-metal silicate, for example water-soluble sodium silicate, soap and sulfonated castor oil (also known as turkey red oil) as the active components, dispersed along with water and adjusted to the proper pH value, excellently fulfills the objectives of this invention. Each of these components, whether individually or in certain limited combinations, has been known and safely used for many years in some type of cleansing product (as noted in the previous reference to *Chemical Formulary*). However, these components previously have not been combined in the manner and amounts taught by the present invention to produce a composition having the described desired properties.

DESCRIPTION OF THE PREFERRED EMBODIMENTS

The soap ingredient should be solid (as opposed to a soft, liquid type) and may be any of several types commonly available, preferably in powder or finely granular form to facilitate dispersion. Typical of these are the sodium soaps of fatty acids derived from tallow, stearin, palm oil, coconut oil, or from the synthetic fatty acids giving soaps of a similar character. An economical and useful soap which has been employed satisfactorily is that known as tallow soap. A preferred soap, whiter in color, nearly odorless, somewhat better performing and almost as low in cost is one made from about 80% tallow and 20% coconut oil.

The sulfonated castor oil is a commercially available product which should be present in an amount of between about 30% and 130%, preferably between about 50% and 100%, and more preferably between about 60% and 100% of the weight of soap used. Sulfonated castor oil has been used for over half a century in textile treatment and dye applications. It also has been employed as a component of abrasive type polishing compounds and other specialties. Within about the last two decades it has found some use in dishwashing liquid formulations based on synthetic detergents. Here it is said to aid in reducing the adverse effect of the synthetic detergents in the dishwater on the skin.

The alkali-metal silicate may be any one of a wide variety of water-soluble silicates of that type (e.g., sodium or potassium silicate) as long as its characteristics permit it to be satisfactorily used in a composition formula. Sodium silicate (the lower in cost) for example, as is well known to those skilled in the soap or cleaning art, is a general term embracing compositions each of which represents ratios of silica to sodium oxide ($SiO_2$:$Na_2O$) falling somewhere between about 1:2 and nearly as high as 4:1, for those considered water soluble. Because of this the illustrative examples following will show the use of specific silicates representing each of two widely differing values of this ratio. The alkalinity of the particular silicate, a function of this ratio, is an important factor in determining the adjustment which must be made to bring the final product within the desired pH range.

It has been found most useful for the purposes of this invention to refer to the theoretically available silica content of the particular silicate to be used. In any of the compositions of the instant invention, this is simply the product of the stated silica content, in percent, of the silicate specified and the weight of that silicate. This figure then can be used to aid in determining the proper quantities of the two other active components of the compositions. A higher ratio of theoretical silica to sulfonated castor oil can be tolerated if the sodium silicate, for example, is high in silica to sodium oxide ratio than if this ratio is low. For example using a silicate of silica to sodium oxide ratio of 3.22:1 we have found that one may employ up to a theoretical silica content of about 60% of the weight of sulfonated castor oil used, particularly as one goes to the higher ratios of sulfonated castor oil to soap, and still have a useful composition. However, it is preferred to keep this percentage below about 40%. If one goes toward the other extreme and uses a sodium metasilicate of about 1:1 silica to sodium oxide ratio, the theoretical silica content of a useful composition is preferably less than about 25% of the weight of sulfonated castor oil used and more preferably between about 10 and 16%, although it may be as low as about 8%. Although it may be done, there is little reason to go to a sodium silicate of higher sodium oxide content.

Sodium silicate solutions having alkalinities falling within the range of about pH 10.8 to 13.4 are commercially available. Solutions made from the solid sodium metasilicate have an even higher pH. In general, the pH is an inverse function of the silica to sodium oxide ratio.

As the pH of the compositions of the instant invention should fall within the range from about 6.5 up to 10 as the practical upper limit, it is convenient to use an acid such as acetic acid to lower the pH of the final mixture of components to the desired value. Other acidic materials, such as propionic acid, citric acid, sodium bisulfate, ammonium dihydrogen phosphate, or phosphoric acid, for example, may be substituted in appropriate amounts, as will be evident to those skilled in the art. Inasmuch as sulfonated castor oil commonly measures about 5 in pH, some compositions using the lesser amounts of a high silica to sodium oxide type of silicate may need no additional acidic material to achieve the final desired pH. If the pH of the final composition exceeds about 10, there is a tendency to cause undesired effects such as excessive dryness, tautness, irritation and possibly cracking of the skin after prolonged contact. The lathering properties of the compositions are excellent down to a pH of about 8. Below a pH of about 6.5 the lathering and some barrier properties are definitely reduced. It is preferred that the pH of the composition be between about 7 and 9, more preferably between about 7 and 8 for the more sensitive skins.

If the water content is varied from about one to about three or more times the weight of soap, the consistency of the product will shift from that of a firm solid to one increasingly soft or fluid. Also, for a given amount of soap, the greater the amount of sulfonated castor oil the softer will the product tend to be. A greater amount of sodium silicate will tend to give a more firm product. If the more liquid consistency is desired, it may be desirable also to replace about 10% or more of the water with ethyl or isopropyl alcohol to reduce the drying time of the composition after it is applied to the skin.

Also, too low a silica equivalent relative to the amount of sulfonated castor oil may cause the product to feel objectionably greasy on the skin. If the percent of sulfonated castor oil and silica relative to soap is too low, or if the ratio of silica to sulfonated castor oil is too high, the barrier properties are adversely affected.

Compositions desirably have the active components comprised of between about 35 and 75 percent soap, 15 and 50 percent sulfonated castor oil, and 4 and 20 percent theoretical silica. In the preferred compositions these percentages are between about 35 and 65 percent soap, 30 and 50 percent sulfonated castor oil and 5 and 15 percent theoretical silica. In the most preferred compositions these percentages are between about 35 and 60 percent soap, 35 and 50 percent sulfonated castor oil and 10 and 15 percent theoretical silica.

The practice of the invention now will be illustrated by the following examples. In the examples the various ingredients are mixed together in the order as listed unless otherwise stated.

EXAMPLE I

| Sodium metasilicate (granular) | 35 g |
|---|---|
| Water | 132 g |
| Sulfonated castor oil | 90 g |
| White vinegar (5% acetic acid) | 135 g |
| Soap (granulated) | 128 g |
| Acetic acid (33%) | 15 g |
| Total | 535 g |

The sodium metasilicate (29% $SiO_2$, the pentahydrate unless otherwise stated) was dissolved by stirring it into the indicated amount of warm water (about 39° to 43° C.), after which the sulfonated castor oil was stirred in, followed by the white vinegar. The batch then was warmed to about 44° to 47° C. at which point the soap granules were stirred in and the batch poured into the bowl of a kitchen-type electric mixer and vigorously stirred while adding the 33% acetic acid and until a light-colored, aerated, homogeneous, thick creamy paste resulted. This was poured immediately into shallow plastic container of about 260 ml. capacity and allowed to cool. The cooled, soft solid product had a pH of about 7 as measured by conventional pH indicator paper. The density of this aerated composition was about 0.7. The active non-soap components total about 78% of the weight of the soap.

EXAMPLE II

| Sodium metasilicate | 35 g |
|---|---|
| Water | 150 g |
| Sulfonated castor oil | 90 g |
| Soap | 105 g |
| White vinegar (5% acetic acid) | 155 g |
| Total | 535 g |

In this example the sodium metasilicate was again dissolved in the warm water and the sulfonated castor oil added as in Example I. The heated batch then was stirred vigorously while adding and dissolving the soap. Only after that was the vinegar added slowly while the stirring continued. The smooth, aerated, homogeneous product was poured into containers to cool, as before. The final cream-white, homogeneous, soft solid product was almost odor-free and had a pH of about 7 as measured by indicator paper. The mixing order followed in this example usually is to be preferred to that employed in the previous example, as being less prone to cause premature separation of solids during the addition of the acid. The active non-soap content is almost 96% of the weight of the soap. The use of white vinegar merely illustrates how a readily available source of acetic acid can be utilized.

EXAMPLE III

In this Example, prepared in a fashion similar to that of Example I, the amount of water was reduced to 88 g. 112 g of 5% acetic acid was used instead of the white vinegar, and 40 g of 5% acetic acid was used instead of the 33% acetic acid. The final aerated, homogeneous soft solid was a bit more firm than that of Example I and had a pH of about 9. With the appropriate corrections for acid content and water content, 33% or some other concentration of acetic acid may be substituted for white vinegar or 5% acetic acid, as will be apparent to those skilled in the art. An even better mixing order is that of Example VI shown later herein.

EXAMPLE IV

| Sodium metasilicate | 35 g |
|---|---|
| Water | 250 g |
| Sulfonated castor oil | 90 g |
| Soap | 128 g |
| Acetic acid 33% | 35 g |
| Household ammonia (ca. 3.3% $NH_3$) | 25 g |

The components were mixed in the same order as listed, the water being warmed to about 43° C. to hasten the solution of the metasilicate. After the addition of the sulfonated castor oil and the soap, the mix was brought up to a temperature of about 70° C. while stirring, then poured into the bowl of a kitchen type electric mixer. Rapid stirring was maintained while the acetic acid and the ammonia were added. The light colored, thick cream-like mix was poured at about 42° to 45° C. into containers to cool and solidify. The pH of the homogeneous, light colored, soft solid measured between about 8 and 9.

EXAMPLE V

| Sodium metasilicate | 44 g |
|---|---|
| Water | 250 g |
| Sulfonated castor oil | 90 g |
| Soap | 128 g |
| Acetic acid 33% | 35 g |

The mixing procedure was the same as in Example IV. The measured pH of the product was about 10, a result of the increased metasilicate content with no corresponding increase in acetic acid. The consistency of this product, although acceptable by this procedure, was improved by continued mixing as the batch cooled to a lower temperature before pouring or by remixing a cooled batch. Some may prefer the softer, less microstructured consistency obtainable by mixing any of the described semi-solid compositions after cooling.

EXAMPLE VI

| Water | 192 g |
|---|---|
| Soap | 135 g |
| Sodium silicate (liquid) | 93 g |
| Sulfonated castor oil | 90 g |
| Acetic acid 33% | 15 g |

This Example illustrates the use of a sodium silicate of a high silica to sodium oxide ratio (3.22:1). The liquid sodium silicate was formally characterized as having 8.90% sodium oxide and 28.7% silica, a density of 1.38, and a pH of 11.3. The quantity used supplied a theoretical silica weight equivalent of almost 20% of the weight of soap. The mixing order was altered from that of the prior examples and the amount of acetic acid was reduced, to adapt to the composition characteristics of this particular sodium silicate. Special care was taken, beginning with the heated soap solution, to insure homogeneous incorporation of each component before slowly adding the next to the batch. Since throughout the mixing procedure the pH was lower than in the previous examples and the ratio of silica to sulfonated castor oil was much greater, this added attention was given. The final product cooled to an excellent, nearly white, homogeneous, stiff paste of pH about 7.5. This composition, is a highly preferred one for its solvent barrier properties, contamination dispersal properties and its satisfactory feel on the skin in humid atmospheres or of users tending to have a more moist skin.

EXAMPLE VII

| | |
|---|---|
| Water | 200 g |
| Soap | 100 g |
| Sodium silicate (liquid) | 100 g |
| Sulfonated castor oil | 100 g |
| Acetic acid 33% | 12 g |

This Example illustrates the use of larger amounts of sulfonated castor oil and 3.22 ratio silicate relative to the amount of soap. The procedure of Example VI was followed and a very smooth product resulted which had barrier properties equal to the excellent ones of the product of Example VI.

Increasing the sodium silicate and sulfonated castor oil to 130 grams each in the formula of Example VII resulted in a very acceptable product but one not quite as smooth in consistency and slightly lower in barrier properties.

If desired, suitable odorants, bactericides, fungicides and/or colorants may be added to the products described herein as will be apparent to those skilled in the art, without departing from the spirit of the instant invention. Similarly, moderate amounts, up to about 10–20 weight percent, of agents such as talc or cornstarch are readily accepted without undue adverse effect on the barrier properties.

The products of each of the examples described herein were stable, homogeneous, easily spreadable dispersions. It was found that these compositions, when applied to the hands and quickly rubbed in until the skin felt comfortably dry, did not transfer deleterious traces to clean surfaces which were incidentally contacted by the protected hands. The composition in each case formed a barely perceptible, effective barrier film or coating on the skin and when subsequently contacted by soil or contaminant prevented direct intimate contact of the skin by the soil and greatly aided the later removal of the soil without using a potentially harmful solvent. At the same time, the compositions maintained the skin comfortably soft and supple. The compositions retained their homogeneous consistency even after months of storage in closed containers.

It has been observed that workers' hands which were dry and cracked and almost impossible to clean properly, because of exposure to inks, paints or lacquers and previous reliance on the use of solvents or prior art protectants, became comfortably supple and crack-free after a period of use of compositions of the instant invention.

A qualitative test and demonstration of the barrier efficacy of products of the instant invention was carried out as follows. A small amount of the composition to be tested was rubbed over a small area on a sheet of white 20 pound bond paper (conveniently a grid of rectangles 1.5 to 3 inches on a side was laid out), simulating the manner in which one would apply it to the hands. The coated paper was dried between about 40° and 46° C. for about 20 minutes. Several drops of each of three common solvents (acetone, paint thinner and lacquer thinner) then were placed on each test area and on the bare paper. The relative speed with which the solvents penetrated or struck through and diffused in the coated paper relative to that on the uncoated paper was noted. The uncoated paper absorbed the solvents almost instantly. Conversely, on the coated paper the solvents formed a tiny pool which persisted for various times before penetration, diffusion and evaporation. Each of over a dozen samples made according to the instant invention teaching and tested thus alongside a prior art soap-sodium silicate-glycerine product resisted the penetration and diffusion of one or more of the three mentioned types of solvents for definitely longer times than did the prior art product. The spots rubbed with the prior art product were quickly penetrated by the solvents which then diffused outward beyond the area covered by the original drops.

As another test the cream or paste composition was rubbed thoroughly onto the hands and fingers. A clean panel of autobody steel was touched with the fingers and the steel surface then spray-painted or brush-painted with dye-colored and pigment-colored enamels which were then allowed to dry. There were no visible signs of defects in the painted surface that may have been caused by transfer of material from the fingers which touched the panel.

A test of highly exaggerated severity was run in the following manner to demonstrate the low degree of surface contamination properties of the compositions of the instant invention: A small amount of the composition was rubbed out on panels of bare and primed autobody steel. These so-treated panels then were spray-painted with lacquer and with urethane enamel and air dried. No visual defects were noted. After the normal bake cycle, all painted areas passed the commonly used pressure-sensitive-tape peelback test for adhesion. When a prior art composition based on soap-sodium silicate-glycerine was tested similarly, the baked urethane enamel over the treated area on primed steel failed the same adhesion test.

Workers applied compositions of the instant invention to their hands and engaged in the usual tasks of mixing dyes and pigments into solvent-based vehicles and of spray-painting articles with such paints. After about two or three hours of such work the hands were pretty well discolored with the paints and dyes. The cream or paste composition was applied again and rubbed over the hands along with water to form a lather which loosened and dispersed the paint and dye which then was rinsed off with water. To the naked eye it appeared that the paint and dye colors were totally removed from the skin. The practice of applying the composition to the hands, working for two or three hours before washing the hands was continued over the normal course of an eight hour day and extended over about two to three weeks. It was found that five to six ounces of the composition lasted about two to three weeks when used by people in the manner described. In each case at the end of the period the skin on the hands was comfortably soft and supple. Some of the same workers previously had used solvents to remove paints and dyes before washing with soap and water. Over a period of time they developed skin cracks and could not completely clean the hands. Some complained of always having the odor of solvent on the hands. After using the cream or paste compositions of the examples over a similar period of time, a normal skin softness returned, cracks diminished or disappeared and the odor of solvent was gone.

All of the compositions of the instant invention serve excellently in the dual role of preapplied and/or postapplied cleansing aids, with those having the higher amounts of sulfonated castor oil relative to soap and moderate to lower amounts of theoretical silica showing somewhat faster action in the latter role on some grease-borne soil.

We claim:

1. A stable, spreadable composition for application to the skin, particularly of the hands, for protecting against and aiding removal of contaminants, comprising:
   the homogeneous product of dispersing in water the active components comprising soap particles, sulfonated castor oil, and a water-soluble alkali-metal silicate, the amount of said silicate being sufficient to provide the theoretical silica equivalent of between about 8 and 60 weight percent of the weight of sulfonated castor oil and the amount of sulfonated castor oil being between about 30 and 130 weight percent of the weight of soap, and acid as needed to adjust the pH to between about 6.5 and 10.

2. The composition as described in claim 1 wherein the product forms a substantially imperceptible film when applied to the skin.

3. The composition of claim 1 in which the H is between about 7 and 9.

4. The composition of claim 1 in which the H is between about 7 and 8.

5. The composition of claim 1 in which the amount of silicate is sufficient to provide a theoretical silica equivalent of between about 10 and 40 weight percent of the weight of the sulfonated castor oil.

6. The composition of claim 3 in which the amount of sulfonated castor oil is between about 50 and 130 weight percent of the weight of the soap.

7. The composition of claim 5 in which the amount of sulfonated castor oil is between about 60 and 100 weight percent of the weight of the soap and the pH is between 7 and 8.

8. The composition of claim 2 wherein the film is removable by the said composition and water.

9. The composition of claim 1 wherein the alkali-metal silicate is sodium silicate.

10. A skin-protective cream comprising:
    the homogeneous product of mixing together water, dry soap, sulfonated castor oil in an amount between about 30% and 130% of the weight of the soap, and water-soluble alkali-metal silicate in an amount sufficient to provide the theoretical silica equivalent of between about 8 and 60 weight percent of the weight of the sulfonated castor oil, and acid as needed to adjust the pH to between about 6.5 and 10.

11. The cream as described in claim 10 wherein said mixture forms a substantially imperceptible removable film when rubbed on and allowed to dry on the skin.

12. The cream as described in claim 10 wherein the alkali-metal silicate is sodium silicate.

13. A skin-protective cream comprising:
    the homogeneous product of dispersing in water three active components, the sum of the said active components being
    (1) between about 35 and 75 weight percent dry soap,
    (2) between about 15 and 50 weight percent sulfonated castor oil, and
    (3) between about 4 and 20 weight percent SiO as water-soluble sodium silicate,
    and acid as needed to make the pH of the product between about 6.5 and 10.

14. The cream as in claim 13 in which the sum of the said three active components comprises
    (1) between about 35 and 60 weight percent soap,
    (2) between about 30 and 50 weight percent sulfonated castor oil, and
    (3) between about 5 and 15 weight percent $SiO_2$ as water soluble sodium silicate.

15. The composition as in claim 13 in which the sum of the three active components is made up of
    (1) between about 35 and 60 weight percent dry soap,
    (2) between about 35 and 50 weight percent sulfonated castor oil, and
    (3) between about 10 and 15 weight percent $SiO_2$ as water soluble sodium silicate.

16. The cream as in claims 10, 13, 14 or 15 in which the pH is adjusted to between about 7 and 9.

17. The cream as in claim 13 wherein the homogeneous product forms a substantially imperceptible film when rubbed on and allowed to dry on the skin, said film being removable by water 18. A skin-protecting and cleaning product, comprising:
    active components comprising soap particles, sulfonated castor oil, and water-soluble alkali-metal silicate dispersed in sufficient water to produce a creamy to semi-solid consistency, and acid as needed to adjust the pH of the product to between about 6.5 and 10.

* * * * *